United States Patent
Desai

(10) Patent No.: US 9,750,839 B2
(45) Date of Patent: Sep. 5, 2017

(54) DRUG ELUTING MEDICAL DEVICES

(75) Inventor: Arpan Desai, Hamden, CT (US)

(73) Assignee: Covidien LP, Mansfield, MA (US)

(*) Notice: Subject to any disclaimer, the term of this patent is extended or adjusted under 35 U.S.C. 154(b) by 959 days.

(21) Appl. No.: 13/429,482

(22) Filed: Mar. 26, 2012

(65) Prior Publication Data

US 2013/0006172 A1    Jan. 3, 2013

Related U.S. Application Data

(60) Provisional application No. 61/502,925, filed on Jun. 30, 2011.

(51) Int. Cl.
| | | |
|---|---|---|
| *A61L 17/14* | (2006.01) | |
| *A61L 17/00* | (2006.01) | |
| *A61L 31/10* | (2006.01) | |
| *A61L 31/16* | (2006.01) | |

(52) U.S. Cl.
CPC ........... *A61L 17/145* (2013.01); *A61L 17/005* (2013.01); *A61L 31/10* (2013.01); *A61L 31/16* (2013.01); *A61L 2300/258* (2013.01); *A61L 2420/08* (2013.01)

(58) Field of Classification Search
CPC ...... A61L 17/145; A61L 17/005; A61L 31/10; A61L 2300/258; A61L 2420/08
USPC .................................. 424/422–426
See application file for complete search history.

(56) References Cited

U.S. PATENT DOCUMENTS

| | | | |
|---|---|---|---|
| 6,391,060 B1 | 5/2002 | Ory et al. | |
| 6,408,656 B1 | 6/2002 | Ory et al. | |
| 6,443,964 B1 | 9/2002 | Ory et al. | |
| 6,451,032 B1 | 9/2002 | Ory et al. | |
| 6,478,727 B2 | 11/2002 | Scetbon | |
| 6,596,002 B2 | 7/2003 | Therin et al. | |
| 6,695,855 B1 | 2/2004 | Gaston | |
| 6,827,966 B2* | 12/2004 | Qiu et al. | 427/2.24 |
| 6,971,252 B2 | 12/2005 | Therin et al. | |
| 7,021,086 B2 | 4/2006 | Ory et al. | |
| 2007/0032805 A1 | 2/2007 | Therin et al. | |
| 2009/0030504 A1* | 1/2009 | Weber et al. | 623/1.42 |

FOREIGN PATENT DOCUMENTS

| | | |
|---|---|---|
| WO | 00/41647 A1 | 7/2000 |
| WO | 02/096477 A2 | 12/2002 |
| WO | 2005/089825 A2 | 9/2005 |
| WO | 2009/158489 A2 | 12/2009 |

OTHER PUBLICATIONS

Search Report from EP Appl. No. 12173984.1 dated Dec. 9, 2013.

* cited by examiner

*Primary Examiner* — Nathan R Price
*Assistant Examiner* — Melissa A Snyder

(57) ABSTRACT

Medical devices possessing coatings are provided. The coatings include at least one polyelectrolyte, capable of changing the surface charge of the device to which they are applied. The polyelectrolytes permit attachment of charged bioactive agents thereto. Multiple polyelectrolytes, possessing opposite charges, may be sequentially applied to produce a medical device having multiple layers. Methods for forming such devices are also provided.

18 Claims, 1 Drawing Sheet

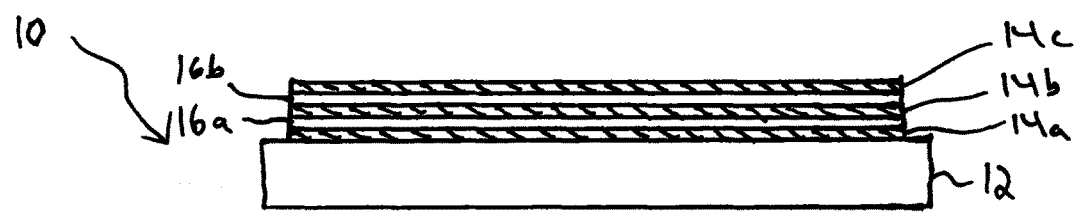

DRUG ELUTING MEDICAL DEVICES

CROSS-REFERENCE TO RELATED APPLICATIONS

This application claims the benefit of, and priority to, U.S. Provisional Patent Application Ser. No. 61/502,925 filed on Jun. 30, 2011, the disclosure of which is hereby incorporated by reference in its entirety.

TECHNICAL FIELD

The present disclosure relates to medical devices suitable for use as drug delivery devices. More particularly, the present disclosure relates to medical devices coated with polyelectrolytes capable of releasing bioactive agents in vivo.

DESCRIPTION OF RELATED ART

Surgical implants, such as drug eluting devices, are known to serve as vehicles for the delivery of drugs or other therapeutic agents. In some cases, devices, such as stents and/or meshes, are coated with a biologically active agent to provide treatment to an implant site. For example, antimicrobial agents may be applied to medical devices to reduce infection and promote healing. Similarly, growth factors may be applied to medical devices to promote healing. The release of the drug from the device may be dependent upon the nature of the attachment of the drug to the device.

Improved medical devices, capable of acting as drug delivery devices, remain desirable.

SUMMARY

The present disclosure relates to medical devices having a substrate possessing a charge, at least one layer comprising a first polyelectrolyte, the first polyelectrolyte possessing a charge opposite the charge on the substrate, at least one layer comprising a second polyelectrolyte, the second polyelectrolyte possessing a charge opposite the charge on the first polyelectrolyte, and at least one bioactive agent. The layers comprising the first polyelectrolyte and the layers comprising the second polyelectrolyte may be in an alternating configuration.

In embodiments, the at least one layer comprising a first polyelectrolyte is disposed on the substrate. Additionally, the at least one layer comprising a second polyelectrolyte is disposed on the at least one layer comprising the first polyelectrolyte. In some embodiments, the substrate possesses a positive charge, the first polyelectrolyte comprises a polyanion, and the second polyelectrolyte comprises a polycation. Alternatively, the substrate possesses a negative charge, the first polyelectrolyte comprises a polycation, and the second polyelectrolyte comprises a polyanion.

The medical device may possess a positive or negative charge, while the bioactive agent may possess a corresponding negative or positive charge. The bioactive agent may be selected from the group consisting of DNA, proteins, growth factors and combinations thereof. The medical device may be a surgical buttress or a hernia mesh.

Alternate embodiments are disclosed herein, in which a medical device includes a substrate possessing a charge, at least one layer comprising a clay platelets, the clay platelets possessing a charge opposite the charge on the substrate, at least one layer comprising a first polyelectrolyte, the first polyelectrolyte possessing a charge opposite the charge on the clay platelets, and at least one bioactive agent. A further embodiment disclosed herein includes a medical device having a substrate possessing a charge, at least one layer comprising a first polyelectrolyte, the first polyelectrolyte possessing a charge opposite the charge on the substrate, at least one layer comprising clay platelets, the clay platelets possessing a charge opposite the charge on the first polyelectrolyte, and at least one bioactive agent.

BRIEF DESCRIPTION OF THE DRAWINGS

FIG. 1 illustrates a medical device of the present disclosure possessing multiple layers of polyelectrolytes.

DETAILED DESCRIPTION

The present disclosure provides medical devices suitable for delivery of bioactive agents. It should be understood that medical device of the present disclosure may be at least partially implanted within a patient, and therefor medical devices disclosed herein also comprise implants. The medical device includes a substrate, to which one or more polyelectrolyte layers are applied.

The medical devices may be fabricated from any biodegradable and/or non-biodegradable material, including polymers, that can be used in surgical procedures. The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body, such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof.

Representative natural biodegradable polymers which may be used to form the medical devices include: polysaccharides such as alginate, dextran, chitin, chitosan, hyaluronic acid, cellulose, gelatin, fucans, glycosaminoglycans, and chemical derivatives thereof (substitutions and/or additions of chemical groups including, for example, alkyl, alkylene, amine, sulfate, hydroxylations, carboxylations, oxidations, and other modifications routinely made by those skilled in the art); catgut; silk; linen; cotton; and proteins such as collagen, albumin, casein, zein, silk, soybean protein; and combinations such as copolymers and blends thereof, alone or in combination with synthetic polymers.

Synthetically modified natural polymers which may be used to form the medical devices include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and combinations thereof.

Representative synthetic biodegradable polymers which may be utilized to form medical devices include polyhydroxy acids prepared from lactone monomers (such as glycolide, lactide, caprolactone, ε-caprolactone, valerolactone, and δ-valerolactone), carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; poly-ortho esters; and copolymers, block copolymers, homopolymers, blends, and combinations thereof.

Synthetic biodegradable polymers also include hydrophilic vinyl polymers including phosphorylcholines such as 2-methacryloyloxyethyl phosphorylcholine, hydroxamates, vinyl furanones and their copolymers, and quaternary ammonia; as well as various alkylene oxide copolymers in combination with other polymers such as lactones, orthoesters, and hydroxybutyrates, for example.

Additionally, polymers such as poly(lactide-co-glycolide)s, polyanhydrides, and polyorthoesters, may be processed such that they have carboxylic groups exposed on the external surface as the surface of the polymer. These bioerodable polymers which may be used herein are referred to as surface eroding polymers.

Other biodegradable polymers include polyphosphazenes; polypropylene fumarates; polyimides; polymer drugs such as polyamines; perfluoroalkoxy polymers; fluorinated ethylene/propylene copolymers; PEG-lactone copolymers; PEG-polyorthoester copolymers; blends and combinations thereof.

Some non-limiting examples of suitable nondegradable materials from which the medical devices may be made include metals, ceramics, and polymeric materials. Suitable nondegradable polymeric materials include, for example, polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; epoxy resins; aramids; rayon; rayon-triacetate; spandex; silicones; and copolymers and combinations thereof.

In accordance with the present disclosure, the substrate utilized to form a medical device of the present disclosure possesses a positive or negative charge. The materials utilized to form the substrate may naturally possess such a charge. For example, dextran naturally possess a negative charge. In other embodiments, the substrate may be functionalized to possess a charge. For example, a positive or negative charge may be introduced onto a substrate using means within the purview of those skilled in the art, including treatments with acids, treatments with bases, introducing functional groups possessing a charge onto a polymeric substrate, combinations thereof, and the like. Still, in other embodiments, a substrate having a negative charge may be modified to have a positive charge, and vice-versa.

At least one polyelectrolyte is applied to the substrate possessing a charge. Where the substrate possesses a positive charge, the polyelectrolyte includes a polyanion. Conversely, where the substrate possesses a negative charge, the polyelectrolyte includes a polycation. In embodiments, multiple layers may be applied to a substrate, by sequential exposure to polyanions and polycations. Thus, for example, where the substrate possesses a positive charge, a first layer applied thereto my include a polyanion. A second layer including a polycation, may then be applied to the first layer. A third layer including a polyanion, which may be the same or different as the polyanion in the first layer, may then be applied to the second layer. A fourth layer, including a polycation, which may be the same or different as the polycation in the second layer, may then be applied to the third layer. The process may be repeated with additional application of alternating polyanion layers and polycation layers, to form a coating possessing multiple layers of polyelectrolytes. Of course, the order of layers would be reversed where the substrate possesses a positive charge.

This sequential application of layers of polyelectrolytes having opposite charges may be referred to, in embodiments, as layer-by-layer deposition, with the resulting coating referred to, in embodiments, as a layer-by-layer coating or a a layer-by-layer film.

Suitable anionic materials for use in forming a polyanionic layer on a substrate include, but are not limited to, heparin, polyacrylic acid, polyvinyl sulfate, dextran sulfate, poly(2-methacryloyloxyethyl phosphorylcholine-co-methacrylic acid), sulfonated polyaniline, gelatin, combinations thereof, and the like. In embodiments, polyacrylic acid or gelatin may be used as the polyanion.

Suitable cationic materials for use in forming a polycationic layer on a substrate include, but are not limited to, chitosan, polydiallyl dimethylammonium chloride, polyamine esters, gelatin, combinations thereof, and the like. In embodiments, gelatin may be used as the polycation.

The above materials for forming the polyanion or polycation layers may also, in embodiments, be utilized to form the substrate to which the layers are applied.

Methods for applying the polyelectrolyte layers to the substrate, as well as any layer previously applied to the substrate, include, but are not limited to, dipping, spraying, brushing, extrusion, film casting and combinations thereof, and the like. In embodiments, a substrate having a charge may be contacted with a first polyelectrolyte possessing an opposite charge, followed by application of a second polyelectrolyte having a charge opposite that of the first polyelectrolyte (and the same charge as the substrate), with the process repeated so that successive layers are applied having a charge opposite to that of the previously applied layer. In this way, layers including the first polyelectrolyte and layers including the second polyelectrolyte are in an alternating configuration.

Thus, for example, in embodiments, a multi-layer coating may be applied to a medical device by dipping a charged substrate into a solution including a first polyelectrolyte possessing an opposite charge, which reverses the surface charge of the medical device. The substrate possessing the first polyelectrolyte may then be dipped into a second solution including a second polyelectrolyte possessing a charge opposite the first polyelectrolyte, which thus again reverses the surface charge of the medical device. By alternating the placement of the substrate in the polyelectrolyte solutions, gradual and controlled formation of electrostatically cross-linked films of polycation-polyanion layers may be formed on the substrate.

In embodiments, a medical device of the present disclosure may possess a substrate and from about 2 layers to about 50 layers of the first polyelectrolyte thereon, in embodiments from about 10 layers to about 30 layers of the first polyelectrolyte thereon, and from about 2 layers to about 50 layers of the second polyelectrolyte thereon, in embodiments from about 10 layers to about 30 layers of the second polyelectrolyte thereon. As noted above, the layers of the first polyelectrolyte and the layers of the second polyelectrolyte may be in an alternating configuration. The total thickness of the polyelectrolyte layers may be from about 10 nm to about 1 micrometer, in embodiments from about 50 nm to about 500 nm, in embodiments from about 80 nm to about 120 nm, in embodiments about 100 nm.

In some embodiments, charged species, including charged nanoparticles, glass beads, clay platelets, metallic alloys, combinations thereof, and the like, may be substituted for one of the polyelectrolytes in forming a charged layer on the substrate.

In accordance with the present disclosure, a bioactive agent may be applied to the surface of the medical device to provide specific biological or therapeutic properties thereto. Any product which may enhance tissue repair, limit the risk of sepsis, and modulate the mechanical properties of the medical device may be coated on the device.

Moreover, the medical device may also be used for delivery of one or more bioactive agents. A bioactive agent as used herein is used in the broadest sense and includes any substance or mixture of substances that have clinical use. Consequently, bioactive agents may or may not have pharmacological activity per se, e.g., a dye. Alternatively a bioactive agent could be any agent that provides a therapeutic or prophylactic effect; a compound that affects or participates in tissue growth, cell growth, and/or cell differentiation; an anti-adhesive compound; a compound that may be able to invoke a biological action such as an immune response; or could play any other role in one or more biological processes. A variety of bioactive agents may be applied to the medical device.

Examples of classes of bioactive agents which may be utilized in accordance with the present disclosure include, for example, anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Other bioactive agents which may be included as a bioactive agent include: local anesthetics; non-steroidal anti-fertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents, such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics, such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anticonvulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; antihistamines; and immunological agents.

Other examples of suitable bioactive agents which may be included in the medical device include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons ($\beta$-IFN, $\alpha$-IFN and $\gamma$-IFN); erythropoietin; nucleases; tumor necrosis factor; colony stimulating factors (e.g., GCSF, GM-CSF, MCSF); insulin; anti-tumor agents and tumor suppressors; blood proteins, such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

In accordance with the present disclosure, the bioactive agent to be applied to the medical device has a charge. Using the methods of the present disclosure, the charge of the surface of a medical device may thus be adjusted so that it is opposite to the charge of the bioactive agent, permitting attachment of the bioactive agent to the medical device due to electrostatic attraction. In embodiments, a bioactive agent having the same charge as a substrate, but different than the charge of the outer-most layer of polyelectrolyte applied to the substrate, may thus be applied to the device and remain thereon due to electrostatic attraction.

Thus, for example, if a medical device is formed of a material having a negative charge, the charge on the surface of the medical device may be changed to a positive charge due to the application of the polyelectrolyte layers as described above, thereby permitting the attachment of negatively charged DNA, proteins, growth factors, and other negatively charged drugs thereto. Conversely, if the medical device has a positive charge, the charge on the surface of the medical device may be changed to a negative charge due to the application of the polyelectrolyte layers as described above, thereby permitting attachment of a positively charged drug, such as insulin, and other positively charged drugs thereto.

In embodiments, one or more of the layers of polyelectrolyte applied to the substrate may be degradable. For example, a polymer such as a polyamine ester, having a positive charge, can be applied to a negatively charged substrate or a previously applied negatively charged polyelectrolyte layer. The ester component renders the layer hydrolytically biodegradable, which may allow for a controlled release of any bioactive agent attached thereto. More specifically, release rates of bioactive agents in situ may be controlled by selecting charged polymers (which contain the bioactive agents) having specified degradation rates.

In other embodiments, drugs may be applied to a layer of any of the polyelectrolytes as they are applied to a substrate. Thus, for example, a substrate having a first charge may be coated with a first polyelectrolyte having an opposite charge, thereby forming a first polyelectrolyte layer thereon. A bioactive agent having a charge opposite the charge of the first polyelectrolyte may be applied to the first polyelectrolyte layer. Depending on the extent of coating with the bioactive agent, a second polyelectrolyte may then be applied to the bioactive agent. Where the bioactive agent forms a complete unitary coating on the first polyelectrolyte layer, the second electrolyte should have the same charge as the first electrolyte, and thus could, in embodiments, be the same as the first electrolyte. Where the bioactive agent forms an incomplete coating on the first polyelectrolyte layer, the second polyelectrolyte may have a charge opposite that of the first polyelectrolyte (and thus the same charge as the bioactive agent) and may be applied simultaneous with the bioactive agent, or subsequent thereto.

In accordance with the present disclosure, multiple bioactive agents may be applied in multiple layers. For example, film layers could be formed incorporating one or more types of growth factors, DNA, analgesics, antimicrobials, etc. The resulting medical device may thus possess multiple layers having one drug, with multiple alternating layers possessing a different drug. For example, the medical device could have 4 layers including a first bioactive agent, and 3 layers containing a second bioactive agent, wherein the second bioactive agent can be tailored to have either a positive or a negative charge. More specifically, certain growth factors can be tailored to have either a positive or a negative charge, and therefor layers can be built up, containing the same growth factor, alternating between a positive and negative charge, therefor delivering more growth factor to the body.

Similarly, the materials utilized to form the polyelectrolyte layers may be formed of polymers with differing rates of degradation, thereby permitting the release of bioactive agents in varying amounts over time. For example, the outer layer could be a quickly hydrolyzing polymer capable of quickly releasing its bioactive agent over a period of from about 1 second to about 6 months, in embodiments from about 30 minutes to about 2 weeks, with a layer under the outer layer formed of a slowly hydrolyzing polymer which releases its bioactive agent over a period of from about 1 second to about 6 months, in embodiments from about 30 minutes to about 2 weeks.

As would be appreciated by one skilled in the art, the use of multiple layers with multiple drugs permits the formation of a drug delivery device having multiple release profiles for multiple drugs.

Medical devices of the present disclosure may be of any type suitable for use within the body. For example, medical devices that may be coated in accordance with the present disclosure include, but are not limited to, meshes, buttresses, tapes, felts, scaffolds, patches, pledgets, tissue reinforcements, sutures, tacks, staples, access devices, catheters, combinations thereof, and the like.

In embodiments, a medical device may be a surgical mesh or similar film. The surgical meshes are suitable for surgical repair of hernias and other surgical procedures requiring reinforcement or repair of soft tissue, such as muscle or wall tissue defects, pelvic organ prolapse, and urinary incontinence, for example. The meshes of the present disclosure can be in the form of sheets, patches, slings, suspenders, and other implants and composite materials such as pledgets, buttresses, wound dressings, drug delivery devices, and the like. The present surgical meshes may be implanted using open surgery or by a laparoscopic procedure.

A surgical mesh in accordance with the present disclosure may be fabricated from monofilament and/or multifilament yarns which may be made of any suitable biocompatible material. Suitable materials from which the mesh can be made should have the following characteristics: sufficient tensile strength to support tissue; sufficiently inert to avoid foreign body reactions when retained in the body for long periods of time; easily sterilized to prevent the introduction of infection when the mesh is implanted in the body; and sufficiently strong to avoid tearing of portions thereof, including any portion through which surgical fasteners may be applied to affix the mesh to tissue.

In some embodiments, the yarns include at least two filaments which may be arranged to create openings therebetween, the yarns also being arranged relative to each other to form openings in the mesh. Alternatively, the mesh may be formed from a continuous yarn that is arranged in loops that give rise to the openings in the mesh. The use of a mesh having yarns spaced apart in accordance with the present disclosure has the advantage of reducing the foreign body mass that is implanted in the body, while maintaining sufficient tensile strength to securely support the defect and tissue being repaired by the mesh. Moreover, the openings of the mesh of the present disclosure may be sized to permit fibroblast through-growth and ordered collagen laydown, resulting in integration of the mesh into the body. Thus, the spacing between the yarns may vary depending on the surgical application and desired implant characteristics as envisioned by those skilled in the art. Moreover, due to the variety of sizes of defects, and of the various fascia that may need repair, the mesh may be of any suitable size.

In embodiments in which at least two filaments form a yarn, the filaments may be drawn, oriented, crinkled, twisted, braided, commingled or air entangled to form the yarn. The resulting yarns may be braided, twisted, aligned, fused, or otherwise joined to form a variety of different mesh shapes. The yarns may be woven, knitted, interlaced, braided, or formed into a surgical mesh by non-woven techniques. The structure of the mesh will vary depending upon the assembling technique utilized to form the mesh, as well as other factors, such as the type of fibers used, the tension at which the yarns are held, and the mechanical properties required of the mesh.

In embodiments, knitting may be utilized to form a mesh of the present disclosure. Knitting involves, in embodiments, the intermeshing of yarns to form loops or interlooping of the yarns. In embodiments, yarns may be warp-knitted thereby creating vertical interlocking loop chains, and/or yarns may be weft-knitted thereby creating rows of interlocking loop stitches across the mesh. In other embodiments, weaving may be utilized to form a mesh of the present disclosure. Weaving may include, in embodiments, the intersection of two sets of straight yarns, warp and weft, which cross and interweave at right angles to each other, or the interlacing of two yarns at right angles to each other. In some embodiments, the yarns may be arranged to form a net mesh which has isotropic or near isotropic tensile strength and elasticity.

In embodiments, the yarns may be nonwoven and formed by mechanically, chemically, or thermally bonding the yarns into a sheet or web in a random or systematic arrangement. For example, yarns may be mechanically bound by entangling the yarns to form the mesh by means other than knitting or weaving, such as matting, pressing, stitch-bonding, needlepunching, or otherwise interlocking the yarns to form a binderless network. In other embodiments, the yarns of the mesh may be chemically bound by use of an adhesive such as a hot melt adhesive, or thermally bound by applying a binder such as a powder, paste, or melt, and melting the binder on the sheet or web of yarns.

The mesh may be a composite of layers, including a fibrous layer as described above, as well as porous and/or non-porous layers of fibers, foams, and/or films. A non-porous layer may retard or prevent tissue ingrowth from surrounding tissues, thereby acting as an adhesion barrier and preventing the formation of unwanted scar tissue. In embodiments, a reinforcement member may be included in the composite mesh. Suitable meshes, for example, include a collagen composite mesh such as PARIETEX™ (Tyco Healthcare Group LP, d/b/a Covidien, North Haven, Conn.). PARIETEX™ composite mesh is a 3-dimensional polyester weave with a resorbable collagen film bonded on one side. Examples of other meshes which may be utilized include those disclosed in U.S. Pat. Nos. 6,596,002; 6,408,656; 7,021,086; 6,971,252; 6,695,855; 6,451,032; 6,443,964; 6,478,727; 6,391,060; and U.S. Patent Application Publication No. 2007/0032805, the entire disclosures of each of which are incorporated by reference herein.

Turning now to FIG. 1, a medical implant 10 is illustrated including a substrate 12, with multiple polyelectrolyte layers disposed thereon. The polyelectrolyte layers have alternating charges, so that if the substrate 12 has a negative charge, layers 14a, 14b and 14c would include a polycation and possess a positive charge, and layers 16a and 16b would include a polyanion and possess a negative charge. Conversely, if the substrate 12 has a positive charge, layers 14a, 14b and 14c would include a polyanion and possess a negative charge, and layers 16a and 16b would include a polycation and possess a positive charge. As noted above, a bioactive agent (not shown) possessing a charge opposite that found on the surface of polyeletrolyte layer 14c may be attached thereto by electrostatic attraction. Moreover, as noted above, bioactive agents (not shown) may also be attached to intermediate layers 14a, 14b, 16a and 16b, where the bioactive agent has a charge opposite the charge of the polyelectrolyte layer to which it is applied. Alternatively, layers comprising the first or second polyelectrolyte may further include a bioactive agent disposed therein.

It will be understood that various modifications may be made to the embodiments disclosed herein. Therefore, the above description should not be construed as limiting, but merely as an exemplification of illustrative embodiments. Those skilled in the art will envision other modifications within the scope and spirit of the present disclosure. Such modifications and variations are intended to come within the scope of the following claims.

What is claimed is:

1. A medical device comprising:
  a substrate possessing a charge;
  at least a first layer comprising a polymer comprising a first polyelectrolyte in combination with at least one bioactive agent, the first polyelectrolyte possessing a charge opposite the charge on the substrate; and
  at least a second layer comprising a polymer comprising a second polyelectrolyte in combination with at least one bioactive agent, the second polyelectrolyte possessing a charge opposite the charge on the first polyelectrolyte,
  wherein an outer layer of the medical device comprises the first layer or second layer, and the outer layer further comprises a polymer capable of releasing its bioactive agent over a period of from about 1 second to about 6 months, with an inner layer comprising the other of the first layer or second layer under the outer layer, the inner layer formed of a polymer which releases its bioactive agent over a period of from about 30 minutes to about 2 weeks.

2. The medical device according to claim 1, wherein the at least one layer comprising a first polyelectrolyte is disposed on the substrate.

3. The medical device according to claim 1, wherein the at least one layer comprising a second polyelectrolyte is disposed on the at least one layer comprising the first polyelectrolyte.

4. The medical device according to claim 1, wherein the substrate is selected from the group consisting of meshes, buttresses, tapes, felts, scaffolds, patches, pledgets, tissue reinforcements, sutures, tacks, and staples.

5. The medical device according to claim 1, wherein the substrate comprises a material selected from the group consisting of collagen, gelatin, polypropylene and polyester.

6. The medical device according to claim 1, wherein the substrate possesses a positive charge, the first polyelectrolyte comprises a polyanion, and the second polyelectrolyte comprises a polycation.

7. The medical device according to claim 1, wherein the substrate possesses a negative charge, the first polyelectrolyte comprises a polycation, and the second polyelectrolyte comprises a polyanion.

8. The medical device according to claim 1, further comprising a charged species selected from the group consisting of nanoparticles, clay platelets, glass beads, metal alloys, and combinations thereof.

9. The medical device according to claim 1, wherein the medical device possesses from about 2 to about 30 layers comprising the first polyelectrolyte, and from 2 about 30 layers comprising the second polyelectrolyte.

10. The medical device according to claim 9, wherein the layers comprising the first polyelectrolyte and the layers comprising the second polyelectrolyte are in an alternating configuration.

11. The medical device according to claim 1, wherein the medical device possesses a positive charge, and the bioactive agent possesses a negative charge.

12. The medical device according to claim 11, wherein the bioactive agent is selected from the group consisting of DNA, proteins, growth factors, and combinations thereof.

13. The medical device according to claim 1, wherein the medical device possesses a negative charge, and the bioactive agent possesses a positive charge.

14. The medical device according to claim 13, wherein the bioactive agent is selected from the group consisting of growth factors, drugs, and combinations thereof.

15. A surgical buttress comprising the medical device of claim 1.

16. A hernia mesh comprising the medical device of claim 1.

17. A medical device comprising:

a substrate possessing a charge;

at least a first layer comprising clay platelets in combination with at least one bioactive agent, the clay platelets possessing a charge opposite the charge on the substrate;

at least a second layer comprising a polymer comprising a polyelectrolyte in combination with at least one bioactive agent, the polyelectrolyte possessing a charge opposite the charge on the clay platelets, wherein an outer layer of the medical device comprising the first layer or second layer releases its bioactive agent over a period of from about 1 second to about 6 months, with a layer comprising the other of the first layer or second layer under the outer layer releasing its bioactive agent over a period of from about 30 minutes to about 2 weeks.

18. A medical device comprising:

a substrate possessing a charge;

at least a first layer comprising a polymer comprising a polyelectrolyte in combination with at least one bioactive agent, the polyelectrolyte possessing a charge opposite the charge on the substrate;

at least a second layer comprising clay platelets in combination with at least one bioactive agent, the clay platelets possessing a charge opposite the charge on the polyelectrolyte, wherein an outer layer of the medical device comprising the first layer or the second layer releases its bioactive agent over a period of from about 1 second to about 6 months, with a layer under the outer layer comprising the other of the first layer or the second layer releasing its bioactive agent over a period of from about 30 minutes to about 2 weeks.

* * * * *